United States Patent [19]

Yelton et al.

[11] Patent Number: 4,816,405

[45] Date of Patent: Mar. 28, 1989

[54] VECTORS FOR TRANSFORMATION ASCOMYCETES

[75] Inventors: M. Melanie Yelton; William E. Timberlake; John E. Hamer, all of Davis, Calif.

[73] Assignee: The Regents of the University of California, Berkeley, Calif.

[21] Appl. No.: 111,091

[22] Filed: Oct. 16, 1987

Related U.S. Application Data

[63] Continuation of Ser. No. 664,230, Oct. 24, 1984.

[51] Int. Cl.[4] .................. C12N 1/20; C12N 15/00; C12N 1/14; C07H 15/12
[52] U.S. Cl. .................. 435/252.33; 435/172.3; 435/254; 435/320; 435/849; 435/913; 536/27; 935/26; 935/29; 935/34; 935/41; 935/68; 935/73; 935/80
[58] Field of Search .............. 435/68, 172.3; 536/320, 536/27; 935/22, 24, 26, 28, 56, 68, 69

[56] References Cited

PUBLICATIONS

Nunberg et al, 1984, "Molecular Cloning and Characterization of the Glucoamylase Gene of *Aspergillus awamori*", *Mol Cell Biol.*, v4 2306–2315.

Berse et al, 1983, "Cloning and Characterization of the Ornithine Carbamoyltransferase Gene from *Aspergillus nidulans*", *Gene*, v 25, 109-117.

Kinghorn et al, 1982, "Cloning and Expression in E. Coli, K–12 of the Biosynthetic Dehydroquinase Function of the arom Cluster Gene . . .", *Mol Gen Gen*, v 186, 145–152.

Maniatis et al, 1982, *Molecular Cloning a Laboratory Manual* Cold Spring Harbor Lab, pp. 45–48.

Yelton et al, 1983, "Developmental Regulation of the *Aspergillus nidulans* trp C Gene", *Proc. Natl. Acad. Sci.*, v 80, 7576-7580 (Dec. 1983).

Yelton et al, 1984, "Transformation of *Aspergillus nidulans*, by using a trp C Plasmid", *Proc. Natl. Acad Sci.*, v 81, 1470-1474.

Tilburn et al, 1983, "Transformation by Integration in *Aspergillus nidulans*" *Gene*, v 26, 205-221.

Hynes et al, 1983, "Isolation of Genomic Clones Containing the Amds Gene of *Aspergillus nidulans*, . . . ", *Mol Cell Bio*, v 3, 1430-1439.

Ballance et al., *Biochem. and Biophys. Res. Comm.* 112(1):284-289, 1983 (Apr. 15).

Primary Examiner—Thomas G. Wiseman
Assistant Examiner—Thomas D. Mays
Attorney, Agent, or Firm—Ciotti & Murashige Irell & Manella

[57] ABSTRACT

Vectors and procedures are provided that enable genetic manipulation of the filamentous ascomycetes such as *Aspergillus nidulans* and *Aspergillus niger*. The systems of the invention permit transformation of various Aspergillus strains as well as the production and secretion of desired foreign proteins. Also provided are cosmid vectors which enable the isolation, cloning, sequencing and modifications of genes from the filamentous ascomycetes.

23 Claims, 4 Drawing Sheets

1

VECTORS FOR TRANSFORMATION OF ASCOMYCETES

This application is a continuation, of application Ser. No. 664,230, filed Oct. 24, 1984 now abandoned.

TECHNICAL FIELD

The invention relates to the recombinant manipulation of a fungal subclass, the filamentous ascomycetes. In particular, the invention relates to vectors, control sequences, and procedures for utilization of various filamentous ascomycete species as transformant hosts and as cellular laboratories for genetic manipulation.

BACKGROUND ART

The ascomycetes comprise a class of fungi which includes among its members a number of useful, familiar, and important eucaryotic organisms. Perhpas the best known among these are the yeast strains which are familiar to all in connection with production of alcoholic beverages and of bakery goods. Other well known representatives include *Neurospora crassa* which is most frequently encountered as a pinkish bread mold, the ringworm which accounts for a formerly more common skin disease, and the blue molds which account for the flavor and appearance of bleu and Roquefort cheese.

The ascomycetes occur in two significantly distinctive types: those which form a filamentous mycelium, the "euascomycetes" and those which do not, the "hemiascomycetes". One authoritative taxonomy of the ascomycetes (never a static classification, however) sets forth five subclasses, four of which are of the first subtype, and one of which is of the second. (Alexopolous, C. et al, *Introductory Mycology* (J. Wiley and Sons, N.Y.).

The subclass hemiascomycetidae, which is of the second type, includes the yeasts such as Saccharomyces and Candida. Genetic manipulation of members of this subclass and methods for transformation thereof, have been relatively well developed (see, for example, Van Solingen, P., et al, *J Bact* (1977) 130:946). Of the remaining subclasses, two contain organisms of industsrial importance: the Plectomycetidae which contains black molds, blue molds, and ringworms, including the various Aspergillus and Penicillium species; and the subclass Pyrenomycetes which is represented by the various organisms causing mildew and by *N. crassa*, and by strains of Trichoderma and of Cephalosporium. While among the representatives of these two filamentous subclasses there are found a wide variety of industrial organisms used for, for example, the production of primary metabolites such as citric acid, of secondary metabolites such as antibiotics, most notably penicillin and cephalosporin and various industrial proteins and enzymes such as proteases and other hydrolytic enzymes, relatively little has been done with respect to the genetics of these organisms. In general they have proved refractory to transformation and to genetic manipulation. Recently, a transformation system has been developed for *N. crassa* (Case, M E., et al, *Proc Natl Acad Sci* (USA) (1979) 76:5259). However, vectors useful for general genetic manipulation even in this species have not been disclosed. More recently, Ballance, D. J., et al, *Biochem Biophys Res Comm* (1983) 112:284 succeeded in transforming *Aspergillus nidulans* (a member of the Plectomycetidae subclass) with a segment of DNA carrying the genes for orotidine-5'-phosphate decarboxylase derived from *N. crassa* (a member of the Pryrenomycetes subclass). However, as the *N. crassa* gene is from a species foreign to the host, the DNA of the transforming plasmid does not integrate into the host genome at a site complementary to an indigenous gene, but rather integrates at a random location, and with relatively low frequency. Also, Tilburn, J et al, *Gene* (19) 26:205 have transformed *A. nidulans* with a plasmid carrying the amdS *A. nidulans* gene. However, this gene, which is expressed to confer phenotypic characteristics including sensitivity to fluoroacetate and ability to grow on acetamide, has been found only in *A. nidulans* strains, and thus may find no indigenous counterparts in the remaining filamentous ascomycetes species.

There is, thus, no currently available system for providing a broad spectrum of tools for genetic manipulation of the important members of the filamentous ascomycetes sublcasses; members such as *Aspergillus nidulans, Aspergillus niger,* plant pathogens, such as Alternaria and Fusarium, and the various Penicillium species, and Cephalosporium species. The present invention provides such systems and tools which enable genetic modification of industrially important strains to perform conversion processes of which they were previously incapable, production and secretion of large quantities of desired foreign proteins by these organisms, and in general, addition of the filamentous ascomycetes to the arsenal of useful recombinant host organisms and gene sources available to the biotechnologist.

DISCLOSURE OF THE INVENTION

The invention relates to systems for genetic manipulation of the filamentous ascomycetes, and to the methods and tools useful in these systems. Vectors are provided that permit the transformation of the various strains of Aspergillus, and that serve as intermediate vectors for ascomycete expression in general. These vectors use DNA control sequences homologous to the host to regulate the expression of a selectable marker in suitable host strains. Also provided are cosmid vectors which permit the isolation, cloning, sequencing, and modification of genes from the filamentous ascomycetes. This permits the cosmids of the invention to be used as shuttles for genetic manipulation of the species or strain furnishing the gene, as well as for the purpose of obtaining large amounts of a desired ascomycete gene.

In a particularly important application and consequence, these cosmid vectors can be used to provide gene sequences from a spectrum of fungal species as sources of signal sequences for the secretion of proteins encoded by selected foreign DNA sequences linked in suitable reading frame. This application is of considerable importance because, in contrast to the yeast representatives of the ascomycetes, the filamentous members are "natural" secreters, i.e., proteins containing suitable signal sequences are expelled into the medium, rather than harbored in the periplasmic space as is the case with yeast.

Thus, the vectors of the invention are useful as intermediates to desired expression vectors for heterologous proteins in ascomycete hosts, as well as serving as shuttles to enable genetic modification of indigenous sequences.

Accordingly, in one aspect, the invention relates to an Aspergillus derived selectable marker for ascomycetes. The invention also relates to control sequences therefor, and to vectors containing these control and marker sequences, along with sequences of bacterial origin. In additional aspects, the invention relates to cosmid vectors which comprise such selectable marker, along with these associated control sequences, bacterial shuttle sequences, and a unique restriction site suitably disposed to accept desired additional ascomycete genomic sequences. In still other aspects, the invention relates to recombinant hosts transformed with these vectors, and to DNA sequences, vectors, and most particularly to genes derived from these vectors. The invention further relates to methods for obtaining genes from filamentous ascomycetes, for modifying such genes and for modifying the genome of filamentous ascomycetes.

MODES FOR CARRYING OUT THE INVENTION

A. Definitions

Figure 1:
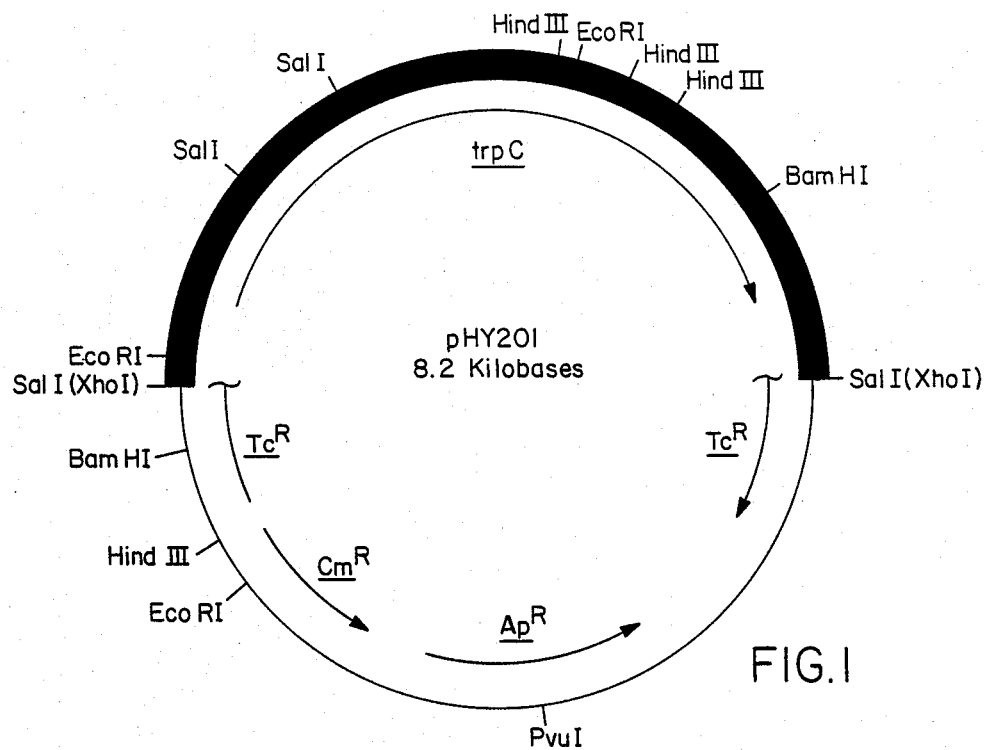
FIG. 1 shows the construction of pHY201.

As used herein, a vector "derived from" another vector refers to a vector which contains DNA sequences or fragments thereof, which are obtained by utilizing the vector of origin suitably treated with restriction enzymes. Thus, vectors derived from pHY201, for example, are those which incorporate portions of DNA (or replications thereof) obtained from pHY201 by treatment with restriction enzymes. They also include vectors formed from DNA sequences rescued from chromosomal DNA of hosts transformed with the vector of origin, e.g., pHY201 as described herein, which recovered DNA contains sequences corresponding to those of the original transforming vector. The definition also includes sequences substantially similar to those of the present vector, though not exactly identical. These might, for example, be obtained by replication of the originating vector sequences with slightly modified primers to effect site directed mutagenesis, or may arise fortuitously. However, such changes, in maintaining substantial similarity to the original sequence, will not materially alter functionality.

"Mutagenically derived from" refers to a subset of such vectors obtained by subjecting a host harboring the vector of origin to substances or conditions which cause mutations in the vector to give desired altered products. One of the utilities of the vectors described herein depends on their suitablility as vectors of origin for such genetic manipulation, especially using bacterial or ascomycete hosts. Thus, vectors "mutagenically derived" from those of the invention are the product vectors of this manipulation.

"Control sequences" refer to DNA sequences which are capable of directing and controlling the expression of an operably linked coding sequence in ascomycetes. As ascomycetes are eucaryotic cells, such sequences include, but are not limited to, promoters and terminators. It is understood that modifications of these sequences may be sufficiently innoccuous to modify the level of, but not to halt entirely, the expression of the coding sequence. Such modifications are also included within the definition of control sequences. (Some modifications may, in fact, enhance the relevant expression level.)

"Cosmid vectors" refers to vectors which contain the cos fragment, thus permitting them to be packaged into λ phage. The origins, and functionality of the cos site sequences are well known in the art. Cosmid vectors of the proper size (i.e., approximately 45–50 kb) are packaged into phage particles using standard techniques and the phage used to infect suitable, for exampple, E. coli, hosts. Phage replication in these transformed hosts results in a high copy number of the DNA comprising the cosmid.

"Vector" is used generically to include plasmids, cosmids, linear transforming DNA, or any other type of DNA sequence capable of transfecting a host. Where a specific type of vector is intended, this will be clear from the context.

"Selectable marker" refers to a DNA sequence which encodes a protein permitting the host organism expressing the sequence to survive on selective media.

"Integration at the homologous site" refers to replacement of a section of genomic DNA with foreign DNA which encodes the analogous protein. Thus, for example, homologous integration of the trpC+ gene, as described herein occurs at the mutated site of the genome containing the modified sequence which would, in the wild type host, have encoded trpC. In order for homologous recombination to occur, the host organism must have a sequence in its genome which is a modified form of the incoming DNA.

"Genes derived from" the cosmids of the inventions refers to genes which are prepared using the cosmids of the invention as intermediates in their preparation.

"Filamentous ascomycetes" refers to those ascomycetes which form a mycelium through a mass of branching, interlocking filaments which, although interrupted by cross walls, permit the passage of cytoplasm between compartments due to perforations in the walls. The filaments thus contain a multiplicity of nuclei in a transportable cytoplasm. Many of these fungi form meiotic spores within a sac when propagated sexually; however, upon proper stimulation, the mechanism of which is not entirely understood, reproduction functions asexually. In this manner of reproduction, condia are borne externally at the tips of budding projections formed at various locations along the filaments. The filamentous ascomycetes which are the basis for the present invention are members of the two subclasses set forth above. As has been mentioned previously, there are two known additional subclasses, but the members of these subclasses are relatively rare as laboratory or industrial organisms, and may or may not be compatible with the techniques and vectors of the present invention. However, the filamentous ascomycetes are clearly differentiated morphologically from the hemiascomycetes, i.e., the yeast containing subclass.

"Transformed" when used herein in the context of transforming a recombinant host, refers to any mechanism whereby DNA transfer may be effected, whether by suitable in vitro transformation techniques sich as calcium phosphate precipitation or calcium ion treatment, transduction by phage infection, conjugation, or other means. "Transform" as used herein simply denotes any process of causing DNA sequences to enter the host.

"Recombinant host" refers to cells that have been, are or will be transformed with DNA sequences prepared by recombinant techniques, and includes the cell originally transformed and, of course, cultures and progeny thereof.

"Genomic library" refers to a collection of DNA sequences which comprises fragments representing substantially the entire set of DNA sequences in a particular genome. These fragments may be simply a digest of chromosomal or genomic DNA or digest fragments cloned into host vectors and includes such materials whether or not transformed into recombinant host cells. The genomic libraries herein may be, harbored in, for example, *E. coli,* or in ascomycetes.

B. General Description

The present invention provides a means for isolating selectable genes from filamentus ascomycetes, inserting them into convenient cloning vectors, and transforming filamentous ascomycete hosts. The vectors of the invention provide a selectable gene, so as to enable homologous integration of the entire plasmid into the host genome, and, further to permit rescue of the plasmid DNA from the genome.

In general, two types of intermediate vectors are central to the present invention. One type, exemplified below by pHY201, comprises a coding sequence along with its control sequences derived from an Aspergillus strain, ligated to bacterial replication and marker sequences. This permits cloning of the vector DNA either in *E. coli,* or by integration into the genome of a filamentous ascomycete host. These vectors, can, in prnciple, be employed as intermediates in the construction of expression vectors for desired coding sequences operable in ascomycete hosts by sequencing the selectable marker gene fragment cloned and isolated, restricting the sequence to eliminate all or part of the coding sequence, placing the desired coding sequence under the control of the promoter and terminating sequences associated with the marker gene, and inserting this package into a cloning vector, such as the intermediate here described, which contains an additional complete gene copy as marker.

A second general type of vector is a comsid which comprises not only the bacterial sequences described above, along with a selectable marker for convenient manipulation, but also a cos site, along with a unique restriction site permitting the insertion of a genomic DNA fragment of the proper size derived from a filamentous ascomycete. This type of intermediate is illustrated herein by pKBY2. Once the appropriate size DNA sequence has been inserted in this intermediate vector, the new, approximately 45-50 kb, vectors can be packaged into λphage for convenient replication as a component of a genomic library. Because the insert fragment is approxiamtely 0.1% of the total sequence length of the genome (35-40 kg out of $2.6 \times 10^7$ base pairs) it can be calculated that about 3000 clones must be screened to have 0.98 probability of obtaining a particular genomic sequence. This, while representing considerable labor, is well within practical limits for obtaining every sequence of the donor genome. An additional advantage is that the genomic stability of the host is not of importance because, since only a few thousand clone need to be screened, reversion is not detectable. Thus, this second type of vector provides a general procedure for obtaining any desired gene from a filamentous ascomycete and cloning it.

Briefly, and in general, the approach is as follows: genomic DNA from the selected filamentous ascomycete is prepared using standard procedure such as those described by Yelton, M., et al, *Proc Natl Acad Sci* (USA) (1984) 81:1470. The genomic DNA is then digested with a restriction enzyme which recognizes frequently occurring sequences. The digestion is done at levels of enzyme and under conditions which will result in a random digestion of the genome. Suitable enzymes would be those which are capable of recognizing and cleaving sequences which occur randomly at intervals of approximately 100-500 bp. The enzymes MboI and Sau3A, exemplified below, which recognize the sequence NGACTN (wherein N represents any one of the four possible nucleotides) are typical of appropriate restriction enzymes. Other appropriate enzymes include MspI, HaeIII, HhaI, and AluI, none of which are overly fastidious as to their recognition sites. Either the enzyme chosen must be compatible with the unique restriction site provided in the intermediate vector to accept the fragments, or linkers must be added to the fragments or to the genomic digest to provide this compatibility. Availability of the linker sequences and methods for obtaining this desired compatibility using them are well established in the art.

The genomic fragments are then ligated into the unique restriction site provided in the intermediate vector. The newly formed appropriately sized cosmids are then packaged into bacteriophage using standard techniques and the resulting phage library used to transduce a convenient host such as an ordinary *E. coli* strain to resistance to an antibiotic marker on the bacterial portion of the plasmid. The resistant transformants can then be grown to obtain the desired quantities of DNA which can be then used to transform a desired filamentous ascomycete host.

The cosmid library obtained by use of the intermediate host cosmid vectors (exemplified below by pKBY2) and the derivative cosmids (exeplified below by those transforming GnI, GnII, and GnIII, or rescued as Cos yAI and Cos yAII) have at least two important utilities. The first relates to placing genes from filamentous ascomycetes into non-indigenous environments to enable manipulation and modification of these genes; the other relates to utilizing the cloned genes as control sequences for the production and secretion of desired heterologous proteins.

With respect to the first utility, advantage is taken of the ability of the isolated gene to be integrated homologously into a recombinant host genome. The desirablity of, and the techniques involved in, this process can best be understood in the context of a hypothetical example. Certain industrial strains of *Aspergillus niger* are capable of syntehsizing antibiotics by, for example, methylation of a particular organic nucleus. It may be desirable to broaden the specificity of this methylase so that additional substrates are capable of being utilized by this enzyme, thus permitting its use in a desired commerically important methylation process. Mutations in the gene encoding the enzyme would be capable of effecting such changes in such specificity of the resulting protein, however, there would be no way prevent mutagens applied directly to the industrial strain from producing, other unwanted effects. This might well prevent the industrial strain harboring the suitably modified enzyme from being useful in the desired conversion process. Generally, industrial strains of microorganisms have been fine-tuned to optimize their growth and metabolic properties so as to obtain the desired amounts of products and suitable economic utilization of nutrients.

Therefore it is necessaryy to be able to mutagenize the desired gene in the absence of the backgrond genomic structure of the host strain. This can be accomplished using the intermediate vectors of the invention. The indutstrial strain genome is digested as described above with a non-fastidious restriction enzyme, and ligated into an intermediate cosmid vector such as, for example, pKBY2, and transformed into a bacterial host, e.g., E. coli. The resulting genomic library is then optionally and preferably selected for the approximately 40 kb fragment containing the coding sequence for the protein desired to be modified. This representative of the library, cloned in, for example, E. coli, is subjected to mutagens in this foreign host. After the desired mutant is obtained, the DNA is recovered and transformed back into the industrial host. Because the plasmid DNA will integrate into the host cell genome at a position homologous to that of the unmutagenized coding sequence, the desired modified DNA is replaced into the industrial strain at the same position as, and in substitution for, the unmodified DNA. It is thus assured that the modification has been selective for the protein of interest.

Alternatively, these and other vectors of the invention can provide a mechanism for genetic modification while the DNA sequence of interest is integrated in to the genome of a substitute host strain. Modification under such conditions may be advantageous in providing a more analogous environment to that of the host wherein the modification will be more realistically related to the desired result. This is possible because the desired mutated sequences can be rescued from the substitute host, replicated in E. coli, and then retransformed into the desired ascomycete strain.

Even the vectors of the first general type (pHY201) discussed hereinabove can be used in this application although the genetic isolation process is less efficient than that enabled by use of the second type (pKBY2) of intermediate vector.

An additional utility of the gene isolating capacity of the cosmid vector sequences (again provided, although less efficiently by the first type of vector set forth herein) relates to the efficient production and secretion of heterologous peptides. Filamentous ascomycetes are efficient and "natural" secretors of certain proteins. The secreted protions because of the structure of the organisms, are transported into the medium rather than retained in the periplasmic space. The secretion takes place through the mediation of suitable signal sequences associated with those proteins naturally secreted by the organisms. Accordingly, using the intermediate vectors of the invention, is possible to obtain complete coding sequences for the signal portions of these peptides and to ligate them to the coding sequences for the desired proteins.

The additional steps begin with obtaining a 35–40 kb fragment containing the gene for a secreted protein. This is exemplified below with respect to the yA gene which encodes p-diphenol oxidase (laccase) an extracelluar enzyme which is conveniently detectable. Mutants lacking the enzyme have yellow spores. This enzyme provides such mutants with the ability to produce green spores, a readily detectable morphological change. Thus recipients of the vector containing the desired fragment can be easily identified. However, by analogous approaches involving mutant recipients deficient in the desired gene, any such gene may be located as part of a 35–40 kb insert.

The vector containing the yA gene is further studied by restriction and sequencing techniques to locate the gene more precisely. These techniques are conventional and are understood in the art. One such technique involves random insertion of a transposon element. Briefly, the retrieved vector is treated with Tn5 according to the procedure of Brujin and Lupski, Gene (19) 27:131–149. Tn5 is a transposon which inserts itself at random locations in a given substrate DNA sequence, destroying the functionality of any gene sequence into which it is inserted. The destruction of the functionality of the yA gene can easily be detected by the failure of mutant Aspergillus nidulans hosts transformed with the plasmid to produce green spores, but rather production of yellow ones. (Successful transformants can, of course, be segregated by an additional marker on the transforming vector; in the case of pKBY2, ability to grow on tryptophan). Once the appropriate vector is found, the location of the insertion can be found by restriction analysis in comparison with untreated plasmids. The untreated plasmids, which still contain the gene intact, can then be sequenced in the indicated location to obtain the entire base sequence of the gene.

Once the gene is located and sequenced, the coding sequence for the p-diphenol oxidase can be excised using standard recombinant techniques and replaced with a coding sequence for the desired heterologous protein, such as, for example, insulin or other hormones, lymphokines, growth factors, or other enzymic or structural proteins. The coding sequence is placed in reading frame with the signal sequence retained in the cosmid. The new cosmid, then containing the desired heterologous coding sequence is then transformed into a filamentous ascomycete host preferably an industrial strain, and cultured to produce and secrete the desired heterologous sequence.

Illustration of the process for preparing these intermediate plasmid and cosmid vectors is set forth in paragraphs C and D below. However, by using comparable procedures, additional marker genes are obtained from strains of Aspergillus which can then be, analogously, cloned into suitable host vectors, such as, for example, pBR322, pUC8 or pUC9, or other commonly available host bacterial vectors. Thus, using the method of this invention there results a series of convenient intermediate cloning vectors capable of transforming Aspergillus or other ascomycetes. Similarily, additional cosmids containing these markers can be prepared, and the entire inventory of the genes of filamentous ascomycetes can be cloned and used as set forth above.

C. An Intermediate Marker Plasmid Construction

The following illustrates the procedure used to prepare the intermediate marker/bacterial vectors of the invention. The illustrated vector pHY201 is a derivative of a commonly available cloning vector, pBR329 and contains a copy of the trpC gene from A. nidulans. The trpC gene encodes a trifunctional polypeptide which has glutamine amidotransferase (GAT), indole glycerol phosphate synthase (IGPS) and posphoribosylanthranilate isomerase (PRAI) activities. These coding sequences are under the control of promoter and terminator sequences operably linked to them.

Briefly, and in summary, the trpC gene was isolated from *A. nidulans* by construction of a λ Charon 4 phage library using a XhoI digest of nuclear DNA from the strain. Selection of the desired phage, λAntrpC12 was made by lytic complementation of *E. coli* MC1066, a strain which is PRAI$^-$.

The selected phage containing the trpC gene was then cleaved with XhoI and the 4.1 kb segment cloned into pBR329 to give pHY201.

pHY201 was successful in transforming *A. nidulans* protoplasts to provide stable transformants, which contained the plasmid DNA integrated into the genome at the trpC$^-$, i.e., the homologous, site. The plasmid DNA could be recovered by isolating transformant genomic DNA, and digestion with XhoI.

C.1. Preparation of the trpC Gene and Construction of pHY201

Nuclear DNA from *A. nidulans* was isolated using a modification of the rapid isolation procedure developed for yeast by Davis, R. W., et al. *Meth Enzymol* (198) 65:404. Flasks containing 50 ml of minimal nitrate medium were inoculated with $5 \times 10^7$ condia from *A. nidulans* strain FGSC4, (obtained from the Fungal Genetic Stock Center, Humboldt State University Foundation, Arcata, CA) and grown at 37° C. with agitation for 48–72 hr. The mycelium was harvested by filtration through Mira-Cloth, washed with cold deionized H$_2$O and frozen and powdered in liqud N$_2$. The cells were rapidly suspended in 5 ml of 50 mM sodium EDTA, pH 8.5, 0.2% SDS containing 5 μl of diethyl oxydiformate and shaken for 1 min at room temperature. The lysate was heated to 68° C. for 15 min, cooled to room temperature, centrifuged for 15 min at 12,000×g, and 4 ml of the supernatant was transferred to a new centrifuge tube. The tube was placed on ice, 0.25 ml of 8.0 M potassium acetate, pH 4.2, was added, and the solutions were mixed thoroughly. After incubation on ice for 1 hr, the tube was centrifuged at 25,000×g at 4° C. for 15 min, 3 ml of the supernatant was transferred to a fresh tube and nucleic acids were precipitated at room temperature by the addition of 3 ml of 2-propanol. The precipitate was collected by centrifugation and dissolved in 0.6 ml of TER [10 mM Tris-HCl, pH 7.6, 1 mM Na$_2$EDTA, 10 μg/ml RNase A (previously heated to 90° C. for 10 min)]. The solution was transferred to a 1.5 ml microcentrifuge tube and the DNA was precipitated at room temperature by the addition of 0.6 ml of 2-propanol and collected by centrifugation for 1 min. The pellet was finally dissolved in 50 μl of TER. Five μl of the DNA solution (1 μg DNA) was used for restriction endonuclease digestions and gel analysis.

The isolated DNA was digested with XhoI and cloned into λCharon 4 phage as desribed by Orr, W. C., et al, *Proc Natl Acad Sci* (1982) 79:5976. Selection of the desired phage was made by lytic complementation of *E. coli* strain MC1066 by the method of Davis, R. W., et al, *Manual for Genetic Engineering: Advanced Bacterial Genetics* (1980) Cold Spring Harbor Laboratory, pp. 142–143. *E. coli* strain K12 MC1066 (Casadaban, M. J., et al, *Methods Enzymol* (1983) 100B:293) requires tryptophan for growth; therefore plaques formed on medium lacking tryptophan were selected. A recombinant phage designated λAnTrpC12, which contains a 4.1 bp XhoI restriction fragment was chosen for further study. This phage contained the entire trpC gene plus approximately 0.4 kb 5' and 3' flanking sequences, as determined by restriction analysis.

The selected phage was digested with XhoI and the 4.1 kb fragment ligated with SalI digested pBR329 (Covarrubias, L L., et al, *Gene* (1982) 17:79) and the litgation mixture transformed into *E. coli* K12 strain HB101 (Boyer, M W., et al, *J Mol Biol* (1969) 41:459). Successful transformants as determined by Amp$^R$Tet$^S$ were screened for the desired 8.2 kb plasmid. the construction of the resulting pHY201 was confirmed by restriction analysis, and is diagrammed in FIG. 1.

C.2. Transformation of *A. nidulans* with pHY201

The utility of pHY201 as an intermediate vector for transforming *A. nidulans* was confirmed by transformation using this vector, and demonstration of integration of the plasmid DNA into the host cell chromosome. Transformation was conducted by preparation of protoplasts followed by treatment with the vector in the presence of a mediating agent, polyethylene glycol (PEG).

C.2.a. Protoplast Preparation

Aspergillus protoplasts were prepared using a modification of the procedures of Peberdy, J. F., et al, *Microbios Letters* (1976) 3:7. Siliconized 1 liter flasks containing 400 ml of minimal medium plus 4 mM filter sterilized L-tryptophan were inoculated with $8 \times 10^8$ conidia of *A. nidulans* strain FGSC237, a strain which lacks GAT, IGPS and PRAI activities, obtainable from the Humboldt State University Foundation supra. The flasks were shaken at room temperature for 18 hours. The mycelium was harvested by filtration through Mira-Cloth, washed with 0.6M MgSo$_4$ and squeezed and blotted wih paper towels to remove excess liquid. The cells were suspended in filter sterilized osmotic medium (1.2M MgSo$_4$, 10 mM sodium phosphate, pH 5.8 ml/g mycelium) by vigorous vortexing, transferred to a 250 ml flask and placed on ice. Filter sterilized solutions of β-glucuronidase (0.2 ml/g mycelium) and Novozyme 234 (20 mg/ml in osmotic medium; 1 ml/g mycelium) were added and the cells were incubated on ice for 5 min. A filter sterilized solution of bovine serum albumin (12 mg/ml in osmotic medium/0.5 ml/g mycelium) was added and the cell suspension was shaken at 80 rpm at 30° C. for 90 min. The suspension was transferred to a centrifuge tube, overlayed with 10 ml of ST (0.6M sorbitol, 100 mM Tris-HCl, pH 7.0) and centrifuged in a swinging bucket rotor at 4,000×g at 4° C. for 15 min. Protoplasts at the buffer interface were removed using a bent Pasteur pipet and placed on ice. The remaining ST was removed, the mycelial pellet was resuspended, fresh ST was added as before, and protoplasts were again banded by centrifugation. The protoplasts were pooled, diluted with 2 volumes of STC (1.2M sorbitol, 10 mM Tris-HCl, pH 7.5, 10 mM CaCl$_2$) and pelleted by centrifugation at 4,000×g at 4° C. for 5 min. They were then washed twice by centrifugation with 10 ml of STC and resuspended in 1/1000 of the original culture volume of STC. Each 400 ml culture yielded $5-10 \times 10^7$ protoplasts, 20–30% of which were capable of regeneration when plated directly onto regeneration medium.

C.2.b. Transformation

The transformation procedure used was a modification of that of Hinnen, A., et al, *Proc Natl Acad Sci* (USA) (1978) 75:1929. DNA, dissolved in 25 μl of STC, was mixed with 100 μl of protoplasts in a disposable plastic centrifuge tube and incubated at room temperature for 25 min. Then 0.2 ml of 60% polyethylene glycol 4000, 10 mM Tris-HCl, pH 7.5, 10 mM caCl₂ was added and the tube was agitated gently by hand. This was followed by a second addition of 0.2 ml and a third addition of 0.85 ml of the polyethylene glycol solution, with gentle mixing after each addition. The protoplasts were incubated for 20 min at room temperature and pelleted at 8,000×g at 4° C. for 5 min. The supernatant was decanted and droplets of solution adhering to the tube were removed with a cottom swab. Th protoplasts were suspended in 2.5 ml of 0.5% yeast extract, 2.0% D-glucose, 1.2M sorbitol and incubated at 37 C. on a rotary shaker at 150 rpm for 2 hr. They were then pelleted at 8,000×g at 4 C. for 5 min, the supernatant was decanted and droplets of medium adhering to the tube were removed with a cotton swab. The protoplasts were finally suspended in 0.15 ml of STC, diluted appropriately in the same buffer, spread onto medium containing 1.2M sorbitol and 1.5% agar and incubated at 37° C. The viability of the protoplasts following these treatments was 1–7%. Plating the protoplasts in agar overlays had no effect on regeneration frequency.

C.3. Confirmation of Plasmid Integration

To select successful transformants, protoplasts treated as set forth in paragraph C.2b. were spread onto a regeneration medium lacking L-tryptophan and inclubated at 37° C. After 12 hr of incubation, small colonies could be seen with the aid of a dissecting microscope, and conidiating colonies were evident after 36 hr. Approximately 20 transformants were obtained per microgram of pHY201 DNA. No colonies were obtained from control protoplasts treated with pBR329 DNA.

Figure 2:
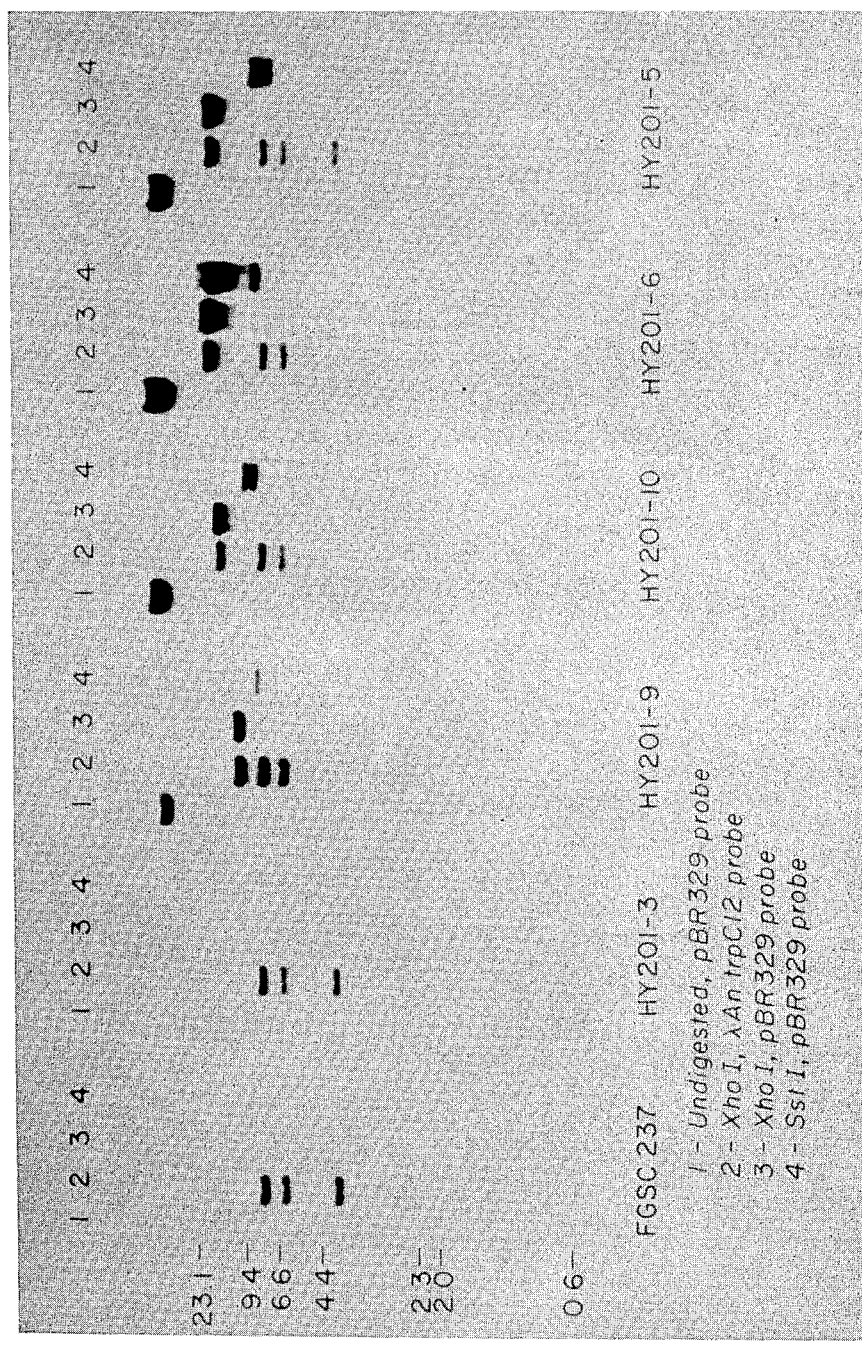
FIG. 2 shows the results of gel electrophoresis of DNA isolated from A. nidulans transformed with pHY201 probed with radiolabeled pBR329 or radiolabeled λAntrp12.

Fifteen transformants were selected and grown in medium lacking L-tryptophan and the total DNA was isolated and subjected to hybridization analysis. Gel blots of undigested, XhoI digested, and SstI digested DNA were probed with either radiolabeled pBR329 or λAnTrpC12 DNA. (Kinasing of the probe DNA was accomplished by nick translation according to the procedures of Rigby, R. W. J., et al, *J Mol Biol* (1977) 113:237; Davis, R. W., et al *Meth Enzymol* (198) 65:404 (Academic Press, NY, NY)). FIG. 2 shows the results obtained from this analysis for five of the transformants.

DNA from host strain FGSC 237, whether undigested or digested with XhoI or SstI, fails to hybridize to kinased pBR329. An apparently successful transformant HY201-3 gave similar results indicating either no integration or subsequent loss of integrated DNA in that case. The remaining transformants yielded integrated DNA hybridizing to pBR329 probe and gave an altered hybridization pattern with respect to λAntrpC12 probe as expected.

In the case of HY201-6 and HY201-10, larger spots were obtained, indicating integration of multiple plasmid copies; HY201-5 showed the integration of two tandem copies of HY201.

Stability of the transformants was verified both for mitosis and meiosis. Mitotic stability was confirmed by growing colonies from single conidia on at least 50 isolates onto selective and non-selective media. All of the colonies remained trp+. Meiotic stability was verified by allowing transformants to self under non-selective conditions and verification that at least 50 colonies derived from single ascospores were trp+. All colonies obtained from HY201-3 were trp+, HY201-6 and HY201-1 resulted in 2% and 12% trpC⁻ segregants respectively.

C.4. Rescue of Integrated DNA

Rescue of pHY201 DNA was also obtained from transformants HY201-9 and HY201-10 by digestion of nuclear DNA with SstI, ligation to circularize, and transformation of *E. coli* MC1066 to Amp$^R$. The resulting successful *E. coli* transformants were also trpC+. Plasmid DNA was isolated from successful transformants using the standard procedure of Maniatis, T., et al, *Molecular Cloning*, supra. Restriction analysis using agarose gel electrophoresis showed several of the recovered plasmids to be identical to pHY201, while others were modified in the trpC coding region.

D. Construction of Intermediate Cosmid Vectors

This paragraph sets forth the preparation of the host cosmid pKBY2. This cosmid was designed to be useful in creating a doubly selective system for obtaining a complete genomic DNA library from filamentous ascomycetes which thus permits the cloning of any desired gene from the donor chromosomal structures. The resulting clone genes are contained in cosmid vectors which are useful for transforming either bacterial or ascomycetes hosts. Accordingly, they are useful as substrate materials which can be transformed into substitute hosts for genetic modification, followed by rescue, then transformation into a target host where they are able to mediate the replacement of a desired sequence by a modified one in this host. They are also useful as sources for signal and control sequences which can be ligated to coding sequences for desired proteins. The resulting fusions may then be used to transform filamentous ascomycetes in order to effect the production and secretion of large amounts of the desired heterologous protein.

D.1 Construction of pKBY2

A plasmid containing the cos site, pJB8 (Ish-Horowicz, D., et al, *Nucleic Acids Res* (1981) 9:2989–2998) was digested with HindIII and SalI and the 2.1 kb fragment containing the cos site isolated. This fragment was ligated to a HindIII/SalI digest of pBR329 and the ligation mixture transformed into *E. coli* HB101 to Amp$^R$-Tet$^S$. The construction of the desired plasmid pKBY0.1 was confirmed by restriction analysis.

pKBY0.1 was digested with SalI, and ligated with the 4.1 kb SalI fragment containing the *A. nidulans* trpC gene prepared as set forth in paragraph C.1. This mixture was transformed into *E. coli* HB101 to Amp$^R$, and the construction of the desired pKBY0.2 confirmed by restriction.

pKBY0.2 was further modified by ligating a BamHI linker obtained from Bethesda Research Laboratories into the NruI site located in the pBR329-derived portion to produce pKBY1.

Figure 3:
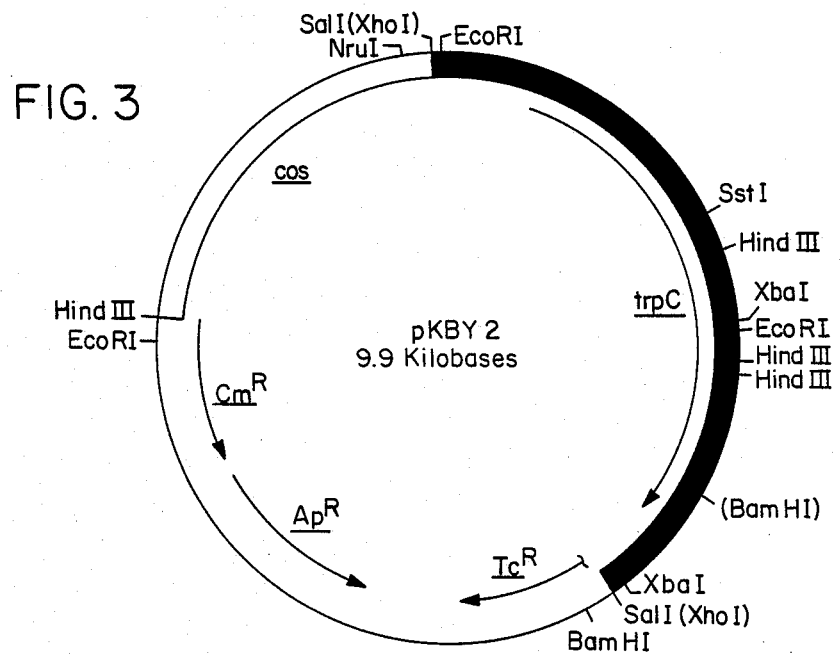
FIG. 3 shows the construction of pKBY2.

To convert pKBY1 to pKBY2, pKBY1 was digested with XbaI to liberate a 1.5 kb fragment, which fragment was replaced by a corresponding modified XbaI fragment from which the internal BamHI site had been removed by sodium bisulfite mutagenesis (Shortle, D., et al, *Proc Natl Acad Sci* (USA) (1978) 75:2170). This ligation mixture was used to transform from *E. coli* HB101 to Amp$^R$. The transformation frequency was similar to that of pHY201 (supra). The construction of pKBY2 was confirmed by restriction analysis to contain the ampicillin and chloramphenicol resistance markers and replication site of pBR329, the modified trpC sequences, the cos site and a unique (BamHI) restriction site adjacent the trpC marker suitable to receive a donor genomic fragment. Fragments produced by digestion of, for example, genomic DNA by BamHI, BglII, MboI or Sau3A can be used directly as donor fragments into this site. pKBY2 is diagrammed in FIG. 3.

D.2. Preparation of an Aspergillus Genomic Library pKBY2 was then used as host vector to obtain a λ phage library of filamentous ascomycetes genes. The gene-containing cosmids were thus selectable through two screens—only ligation products which incorporated the proper size genomic fragments are incorporated into phage so as to become infective against $E.$ $coli$, and only ligation products containing the trpC marker were successful in providing the infected bacteria with metabolic systems needed to grow in the absence of trptophan.

Nuclear DNA was isolated from $Aspergillus\ nidulans$ strain FGSC4 (Glasgow Wild Type) by the method of Davis, et al described in paragraph C.1. Five 40 μg samples of isolated DNA were treated with varying amounts of MboI to yield digestion products ranging in size from 0.5-70 kb. The reaction mixtures were combined and subjected to sucrose density gradient ultracentrifugation as described by Maniatis, el al, $Cell$ (1978) 15:687-701 to obtain fractions containing 30-50 kb fragments as verified by agarose gel electrophoresis. The 30-50 kb fragments were precipitated by additionn of 2.5 volumes of 95% ethanol, collected by centrifugation, washed twice with 70% ethanol, dried and resuspended in TC buffer (10 mM Tris-HCl, pH 7.5, 1 mM EDTA). The DNA was precipitated and washed and resuspended in TC buffer at a concentration of 400 μg/ml.

One ml of this suspension (4 μg fragments) was mixed with 1 μg BamHI-digested, dephosphorylated pKBY2 DNA in 20 μl (final volume) of standard ligation buffer and ligated for 18 hours at 15° C. Samples of the ligation reaction (4 μl) were treated with bacteriophage in vitro packaging extract (Amersham) using the procudures recommended by the supplier. The reaction mixtures were combined, serially diluted and used to transduce $E.\ coli$ HB101 to $Amp^R$. The results indicated that $1.5 \times 10^5$ encapsidated cosmids were produced.

To obtain the genome containing cosmids, approximately 4,000 $Amp^R$ transductants were grown in 20×10 cm Petri dishes. A heavy suspension of cells from each of 15 of these transformants was prepared in L-broth containing 100 μg/ml ampicillin and used to inoculate 1 l of the same medium to an $OD_{600}=0.1$. The cells were grown at 37° C. to an $OD_{600}$ of 0.6, spectinomycin (50 μg/ml) was added and the culture incubated for an additional 12 hours. Cosmid DNA was isolated using the procedure of Clewell, D. B., et al, $Proc\ Natl\ Acad\ Sci$ (USA) (1969) 62:1159-1166.

The isolated cosmids were found to have an average size of cloned fragment of 35-40 kb as judged by electrophoretic analysis of EcoRI digestion products; each contained a different insert. Thus about 800 cosmids from the library are equivalent to the size of the $A.\ nidulans$ genome.

(The EcoRI pattern of an amplified sample of the entire library differed from that of nuclear DNA obtained from the $A.\ nidulans$ source strain, indicating a non-random amplification of some clones.)

D.3. Expression in Transformed Ascomycete Hosts

D.3.a. Expression of the yA2 Gene

The presence of the yA2 and pabaA1 genes on the resulting cosmids was confirmed by transformation of the yellow spored $A.\ nidulans$ strain FGSC237 (supra) (yA2−, pabaA1−, trpC 801) to trpC+ using cosmid library DNA. Ten samples of protoplasts derived from the strain were treated with 10 μg cosmid DNA under the protocol set forth in paragraph C.2, and plated separately. 100 trpC+ transformants were yielded by each plate, three plates produced single, green-spored colonies which presumably, then, are yA+ transformants. (Controls using pKBY2 DNA gave transformants which were all yellow spored.) All three of the green spored colonies retained the pabaA1 marker of the recipient strain, i.e., they were unable to grow in the presence of p-aminobenzoic acid.

These transformants were designated GnI, GnII, and GnIII, and were purified by two cycles of single spore isolation on medium lacking trytophan before subjecting them to further analysis. These transformants were characterized as set forth in ¶D.3.b, and the cosmid DNA rescued as set forth in ¶D.3.c.

D.3.b. Chromosomal Integration of pKBY2 Containing yA

Figure 4:
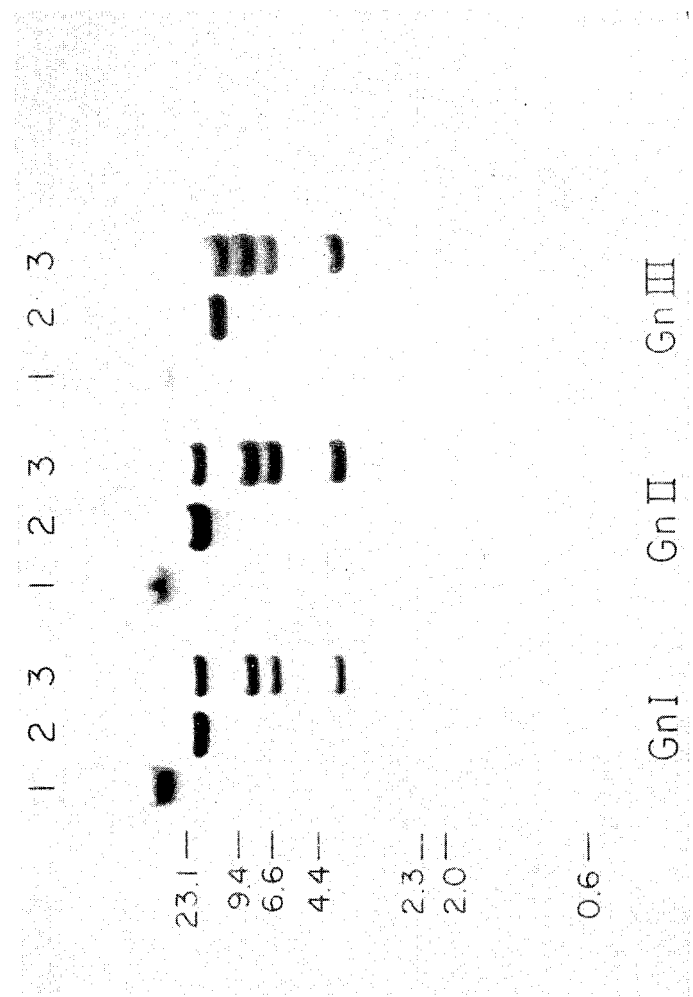
FIG. 4 shows the results of gel electrophoresis of DNA isolated from A. nidulans transformed with pKBY2 probed with radiolabeled pBR329 or radiolabeled λAntrop12.

Total DNA was isolated from each of the three green spored transformants of ¶D.3.a which had been grown in medium lacking L-tryptophan, and gel blots of undigested and XhoI digested DNA were probed with labeled pBR329 and with λAntrpC12, according to the procedures set forth in ¶C.3. (λAntrpC12 hybridizes with the 4.1 kb XhoI fragment containing the trpC gene as well as with two adjacent 6.3 and 7.9 kb XhoI fragments). The results are shown in FIG. 4.

Undigested DNA from all transformants hybridized wih pRB329 at the same position as did chromosomal DNA, thus showing that vector DNA was integrated into the chromosome. XhoI digestion gave, in all cases, a single large >10 kb fragment that hybridized to pBR329, which was smaller in the DNA from GnIII than in DNA from GnI and GnII. λAntrpC12 DNA hybridized with the expected XhoI fragments from the chromosome as well as with the same large fragment as hybridized to pBR329. All of the spots were of approximately such intensity, as to be consistent with one additional copy of the trpC gene per cell. The presence of an unaltered 4.1 kb XhoI fragment in the transformants shows that the transforming DNA had not integrated into the resident trpC gene.

The presence of the protein product of the yA gene, conidial laccase, in the transformants was confirmed by testing protein extracts for enzymatic activity and for cross reactivity with laccase anti-serum.

D.3.c. Rescue of yA Cosmid DNA

Samples (0.2-0.5 μg) of total DNA from each green spored transformant was subjected to in vitro packaging as set forth in paragraph D.2 above, and samples of the packaging reaction used to transduce $E.\ coli$ HB101 to $Amp^R$. Packaged DNA from GnI and GnII transformants yielded 2400 and 80 $Amp^R$ colonies respectively; GnIII yielded only a single slow growing colony.

Figure 5:
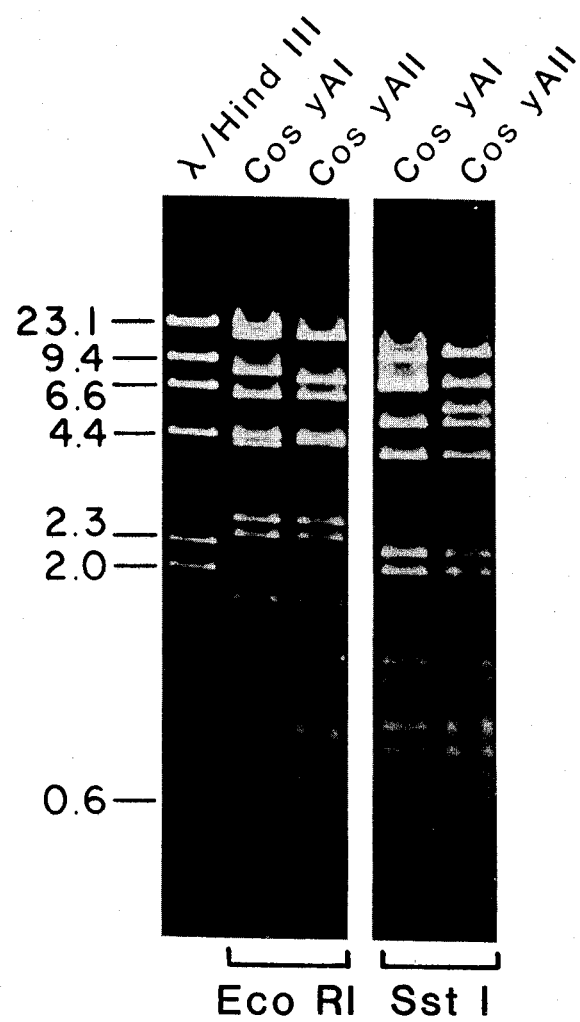
FIG. 5 shows the EcoRI and SstI restriction patterns of Cos yAI and Cos yAII.

Several GnI and GnII transductants were colony purified, and cosmid DNA was isolated and subjected to restriction analysis. All cosmids recovered from GnI yielded indistinguishable electrophoretic patterns following digestion with EcoRI or with SstI as did all cosmids from GnII. One cosmid from each class was chosen and designated Cos yAI and Cos yAII (from GnI and II transductants, respectively). FIG. 5 shows the EcoRI and SstI restriction patterns of Cos yAI and Cos yAII DNA, which shows that the two cosmids contained highly related but distinguishable approximately 35 kb inserts, indicating the selectivity of the cloning procedure.

Nuclear DNA from *A. nidulans* FGSC237 digested with EcoRI or SstI was hybridized with Cos yAI and Cos yAII to give patterns consistent with that of FIG. 5, demonstrating that the inserts were derived from Aspergillus and that the sequences were unique in the genome at the hybridization criterion employed (0.036 m Na+, 68° C.).

Both Cos yAI and Cos yAII transformed *A. nidulans* FGSC237 to tryptophan prototrophy at a frequency similar to that obtained with pKBY2, and most expressed the yA gene. Of 75 trpC+ transformants obtained, 64 (85%) produced green conidia.

D.3.d. Expression of pabaAI

A suspension of spores from the trpC+ colonies obtained from transformation of *A. nidulans* FGSC237 with the cosmid library DNA of ↿D.2 were selected for pabaA+. The pabaA2 allele reverts at a frequency of $<4\times10^7$. Four pabaA+, yA2; trpC+ colonies were selected, purified by two cycles of single spore isolation and total DNA was prepared. Analysis of gel blots showed that each isolate contained pKBY2 DNA sequences in an unaltered, 4.1 kb XhoI fragment containing the trpC801 allele, as was the case with the green-spored transformants. DNA from two of these strains was subjected to in vitro λ packaging, and samples were used to transduce *E. coli* HB101 to Amp$^R$. Cosmids were recovered in both cases and had indistinguishable electrophoretic patterns following digestion with EcoRI or with SstI, indicating that they were obtained as a result of positive selection.

On 22 Oct. 1984, Applicants have deposited with the American Type Culture Collection, Rockville, MD, USA (ATCC) pHY201 in the host *E. coli* HB101, ATCC accession no. 39899, and, pKBY2 in *E. coli* HB101, ATCC accession no. 39898. This deposit was made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organism will be made available by ATCC under the terms of the Budapest Treaty, and subject to an agreement between Applicants and ATCC which assures unrestricted availability upon issuance of the pertinent U.S. patent. Availability of the deposited strain is not to be construed as a license to practice the invention in contravention of the rights granted under the authority of any government in accordance with its patent laws.

We claim:

1. A vector effective in transformation of a bacterial or filamentous ascomycete host which vector comprises:
   (a) a DNA sequence comprising the Aspergillus trpC gene; and
   (b) replication and marker sequences from a pBR329 or derivatives thereof.

2. The transformation vector of claim 1 which is pHY201 or a derivative thereof.

3. A recombinant expression vector for a desired coding sequence placed under the control of said trpC gene of claim 1, and wherein said coding sequence is operable in a species of an ascomycete.

4. A recombinant expression vector for a desired coding sequence placed under the control of said trpC gene of claim 1, and wherein said coding sequence is mutagenically derived and operable in a species of ascomycete.

5. A recombinant bacterial or ascomycete host transformed with the vector of claim 1.

6. A recombinant bacterial or ascomycete host transformed with the vector of claim 3.

7. A recombinant bacterial or ascomycete host transformed with the vector of claim 4.

8. A cosmid vector or a derivative thereof which comprises:
   (a) a DNA sequence comprising the Aspergillus trpC gene,
   (b) replication and marker sequences operable in a bacterial host; and
   (c) a unique restriction cleavage site external to the gene of (a).

9. The vector or derivative of claim 8 wherein the restriction cleavage site of (c) is complementary to cleavage products of a restriction enzyme which randomly cuts filamentous ascomycete DNA at intervals of approximately 100–500 bp.

10. The vector or derivative of claim 8 which is pKBY2.

11. The vector or derivative of claim 8 which further includes a 30–45 kb fragment of genomic DNA derived from a species of filamentous ascomycete.

12. A recombinant bacterial or ascomycete host transformed with the vector or derivative of claim 11.

13. A genomic library from a filamentous ascomycete which comprises 30–45 kb fragments of the genome of said ascomycete inserted into the cosmid vector of claim 8.

14. The library of claim 13 transformed into a recombinant bacterial or ascomycete host.

15. The vector or derivative of claim 11 wherein the fragment of genomic DNA includes the yA2 gene.

16. The vector or derivative of claim 11 wherein the fragment of genomic DNA includes the pabaA gene.

17. The vector or derivative of claim 11 which is Cos YAI or Cos yAII.

18. A filamentous ascomycete gene derived from the vector of claim 11.

19. The sequence of claim 1 which is a 4.1 bp XhoI restriction fragment of λAnTrpC12.

20. The vector or derivative of claim 8 wherein the bacterial host is *E. coli*.

21. The host of claim 12 which is *E. coli*.

22. The host of claim 12 which is an Aspergillus strain.

23. The host of claim 22 which is *A. nidulans*.

* * * * *